United States Patent [19]

Sangokoya

[11] Patent Number: 5,041,583
[45] Date of Patent: Aug. 20, 1991

[54] PREPARATION OF ALUMINOXANES
[75] Inventor: Samuel A. Sangokoya, Baton Rouge, La.
[73] Assignee: Ethyl Corporation, Richmond, Va.
[21] Appl. No.: 544,878
[22] Filed: Jun. 28, 1990
[51] Int. Cl.$^5$ ............................................... C07F 5/06
[52] U.S. Cl. .................................................... 556/179
[58] Field of Search .......................................... 556/179

[56] References Cited
U.S. PATENT DOCUMENTS

| | | | |
|---|---|---|---|
| 4,404,344 | 9/1983 | Sinn et al. | 526/160 |
| 4,544,762 | 10/1985 | Kaminsky et al. | 556/179 |
| 4,665,208 | 5/1987 | Welborn et al. | 556/179 |

FOREIGN PATENT DOCUMENTS

| | | | |
|---|---|---|---|
| 0208561 | 1/1987 | European Pat. Off. | 556/179 |
| 3240383 | 5/1984 | Fed. Rep. of Germany | 556/179 |
| 89-02453 | 3/1989 | PCT Int'l Appl. | 556/179 |

OTHER PUBLICATIONS

Handbook of Chemistry and Physics, 63rd Edition, CRC Press, 1982–1983, pp. B-87, B-90, B-116, B-133, B-148.
Catalog Handbook of Fine Chemicals, Aldrich Chemical Company, Inc., 1990–91, pp. 116, 254, 272, 801, 809, 1092–1093, 1166–1167.
Ueyama et al., Inorganic Chemistry, 12, No, 10, 2218 (1973).
Aoyazi et al., Inorganic Chemistry, 12, No. 11, 2702 (1973).
Herwig, J., Dissertation, pp. 18–25, 94–97, University of Hamburg, 1979.

Primary Examiner—Arthur C. Prescott
Assistant Examiner—Porfirio Nazario
Attorney, Agent, or Firm—David M. Bunnell

[57] ABSTRACT

Hydrocarbylaluminoxanes such as methylaluminoxanes are prepared by reacting a hydrocarbylaluminum compound with a hydrate of an alkali or alkaline earth metal hydroxide.

12 Claims, No Drawings

PREPARATION OF ALUMINOXANES

BACKGROUND

This invention relates generally to a process for preparing aluminoxanes and more specifically to the preparation of aluminoxanes, such as methylaluminoxane, by reacting a hydrocarbyl aluminum compound with a hydrate of an alkali or alkaline earth metal hydroxide such as lithium hydroxide monohydrate.

Vandenberg, U.S. Pat. No. 3,219,591, reported the catalytic activity of compounds formed by the reaction of trialkyl aluminum with limited amounts of water in the polymerization of epichlorohydrin and other oxiranes. Shortly thereafter Manyik et al., U.S. Pat. No. 3,242,099, reported the use of aluminoxanes, made by reacting 0.85–1.05 moles of water with hydrocarbyl aluminum compounds such as triisobutyl aluminum, as co-catalysts with certain transition metal compounds in the polymerization of mono-unsaturated α-olefins; e.g. ethylene and propylene. Isobutylaluminoxane was also made by adding an equal mole quantity of water to a heptane solution of triisobutyl aluminum.

Manyik et al. U.S. Pat. No. 3,300,458 prepare alkylaluminoxane by passing a hydrocarbon through water to form a wet hydrocarbon and mixing the wet hydrocarbon and an alkyl aluminum/hydrocarbon solution in a conduit.

Schoenthal et al. U.S. Pat. No. 4,730,071 show the preparation of methylaluminoxane by dispersing water in toluene using an ultrasonic bath to cause the dispersion and then adding a toluene solution of trimethyl aluminum to the dispersion. Schoenthal et al. U.S. Pat. No. 4,730,072 is similar except it uses a high speed, high shear-inducing impeller to form the water dispersion.

Edwards et al. U.S. Pat. No. 4,772,736 describe an aluminoxane process in which water is introduced below the surface of solution of hydrocarbyl aluminum adjacent to a stirrer which serves to immediately disperse the water in the hydrocarbon solution.

The preparation of alkyl aluminoxanes from $R_2AlOLi$, formed by reacting $AlR_3$ and anhydrous lithium hydroxide, and $R_2AlCl_2$ has been reported in the literature, for example, Ueyama et al., Inorganic Chemistry, 12, No. 10, 2218 (1973) and Aoyazi et al., Inorganic Chemistry, 12, No. 11, 2702 (1973).

Sinn et al. U.S. Pat. No. 4,404,344 prepare methylaluminoxane by adding trimethyl aluminum to a slurry of $CuSo_4.5H_2O$ in toluene. Introducing water as a metal hydrate controls its reactivity with the trimethyl aluminum. Kaminsky et al. U.S. 4,544,762 is similar except it uses an aluminum sulfate salt hydrate to supply the water. Likewise, Welborn et al. U.S. 4,665,208 describe the use of other metal salt hydrates such as $FeSo_4.7H_2O$ as a water source in preparing aluminoxane. Substantial loss of aluminum values usually results when using salt hydrates (acid-base products).

I have now discovered a process for making hydrocarbylaluminoxanes using hydrates which greatly reduces the loss of aluminum values.

SUMMARY OF THE INVENTION

In accordance with this invention, there is provided a process for preparing a hydrocarbylaluminoxane comprising reacting a hydrocarbylaluminum compound with a hydrate of an alkali metal hydroxide.

DETAILED DESCRIPTION

Hydrocarbylaluminoxanes may exist in the form of linear or cyclic polymers with the simplest compounds being a tetraalkylaluminoxane such as tetramethylaluminoxane, $(CH_3)_2AlOAl(CH_3)_2$, or tetraethylaluminoxane, $(C_2H_5)_2AlOAl(C_2H_5)_2$. The compounds preferred for use in olefin polymerization catalysts usually contain about 4 to 20 of the repeating units:

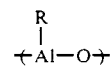

where R is $C_1$–$C_8$ alkyl.

The hydrates which are useful in the invention include hydrates of alkali or alkaline earth metal hydroxides such as, for example, lithium, sodium, potassium, barium, calcium, magnesium, and cesium hydroxides. These compounds can form hydrates which readily lose water which permits the reaction to be carried out at room temperature or below. For example, sodium hydroxide mono- and dihydrate, barium hydroxide octahydrate, potassium hydroxide dihydrate, cesium hydroxide monohydrate and the like. Especially preferred is $LiOH.1H_2O$ which is a well defined monohydrate. It is believed that these hydroxide hydrates differ from salt hydrates (acid-base products) in that the water of hydration is more loosely bound through hydrogen bonding.

Any hydrocarbyl aluminum compound capable of reacting with the hydrate to form an aluminoxane can be used. This includes, for example, trialkyl aluminum, triaryl aluminum, mixed alkyl aryl aluminum, and the like.

The preferred aluminum compounds are the alkyl aluminum compounds, especially trialkyl aluminum compounds such as trimethyl aluminum, triethyl aluminum, triisobutyl aluminum, tri-n-hexyl aluminum, trioctyl aluminum and the like. Of these, the more preferred are the tri-$C_1$–$_4$-alkylaluminum compounds.

Of the various hydrocarbyl aluminoxanes, methylaluminoxane and ethylaluminoxane are the more difficult to prepare because of the extreme reactivity of trimethyl aluminum and triethyl aluminum with water. The most reactive is trimethyl aluminum and accordingly the most preferred embodiment is the application of the process to make methylaluminoxane.

The reaction is carried out in an inert solvent. Any inert solvent can be used. The preferred solvents are aliphatic and aromatic hydrocarbons. Aromatic hydrocarbons are more preferred such as toluene, xylene, ethylbenzene, cumene, mesitylene and the like. The most preferred solvent is toluene.

The concentration of the hydrocarbyl aluminum compound in the inert solvent can range from about 1–30 weight percent. A preferred concentration is about 5–20 weight percent, more preferably 10–15 weight percent.

The mole ratio of aluminum compound to alkali or alkaline earth metal hydroxide hydrate can vary widely such as, for example, from 2:1 to 1:2. Ratios of about 2 moles of aluminum compound to about 1.5 moles of monohydrate are preferred.

Unlike the reactions of prior art salt hydrates which require heating to temperatures of 70° C. or more, and usually are accompanied by a 40–60% loss of Al values, the process of the invention can be carried out at room temperature or below. This reduces the loss of aluminum values to as low as 10 to 15 percent. The minimum temperature is that at which the reaction will proceed and the maximum temperature is selected to optimize the yield of aluminoxane without excessive loss of aluminum values. Suitable temperatures range, for example, from about −20° C. to 60° C. with about −5° C. to 40° C. being preferred. Representative reaction times depend upon the reaction temperature and aluminum alkyl concentration, for example, typically from 1 to 20 hours or more.

The process produces high yield of soluble hydrocarbylaluminoxane which has good selective activity as a catalyst component for olefin polymerization.

The invention is further illustrated by, but is not intended to be limited to, the following examples. All experiments were carried out under inert atmosphere conditions, using Schlenk glassware and vacuum line, in conjunction with a $N_2$-dry box. Solvents were dried using standard methods. Filtration and vacuum distillation were done inside the $N_2$-dry box and distillates collected in a trap at −78° C.

EXAMPLE 1

Trimethylaluminum (TMA) (15.0 g, 0.20 mol) was dissolved in toluene (200 ml). The solution was cooled to −20° C. and then $LiOH.1H_2O$ (4.4 g, 0.10 mol) was added. Gas evolution was very slow at this point. The mixture was allowed to warm slowly to 0° C. (within 30 minutes) and then kept at this temperature for about 20 hours. The slurry was filtered and the solid residue was washed with toluene. The clear filtrate and washings were combined and analyzed for soluble aluminum content. Analysis showed that 85% of the original aluminum content remained in the resulting solution product.

EXAMPLE 2

TMA (15.0 g, 0.20 mol) was dissolved in toluene (200 ml) and $LiOH.1H_2O$ (6.6 g, 0.16 mol) was slowly added at room temperature, in batches, over about 15 minutes. The reaction was exothermic, and the temperature of the mixture rose to 55° C. within 30 minutes. As the temperature started to cool down, the slurry was filtered and the residue was washed with toluene. The clear filtrate and washings were combined and analyzed for soluble aluminum content. The solution (204 g) was found to contain 2.28 wt % Al which is equivalent to 86% of the initial aluminum content.

EXAMPLE 3

TMA (15.0 g, 0.20 mol) was dissolved in heptane (80 ml) and then $LiOH.1H_2O$ (4.4 g, 0.10 mol) was added slowly at room temperature over a period of about 1 hour. Gas evolution was vigorous, but the reaction was only slightly exothermic (unlike the reaction in toluene). The reaction temperature rose to 35° C. before starting to cool down. The mixture was stirred for about 2.5 hours and then filtered. The solid residue was washed with heptane. The combined washings and filtrate (100 g) analyzed for 4.80 wt % Al, which is equivalent to 89% of the initial aluminum content.

EXAMPLE 4

This preparation was carried out as described in Example 2, except that the mixture was stirred for a longer period (4.5 hours). The combined filtrate and washings contained 0.142 mol of Al, which is 71% of the original aluminum content.

EXAMPLE 5

This preparation was carried out as described in Example 2, except that instead of a 4:3 molar ratio (TMA/$LiOH.1H_2O$) an equimolar of TMA and $LiOH.1H_2O$ was employed. The reaction was completed in about 2 hours. The combined filtrate and washings (266 g) contained 1.55 wt % of Al which is equivalent to 76.5% of the initial aluminum used.

EXAMPLE 6

Methylaluminoxane (MAO) prepared according to Example 1 was used in the polymerization of ethylene. Dry toluene (750 ml) was charged to a one liter autoclave which had been heated and purged with nitrogen for at least one hour. The toluene solution of aluminoxane (7 mmoles Al) was added and the system was heated to 80° C. A freshly prepared solution of bis(cyclopentadienyl)zirconiumdichloride ($Cp_2ZrCl_2$) containing 0.34 mmoles was added. The reactor was then pressurized to 60 psi with ethylene.

Polymerization was conducted for ten minutes, after which the polyethylene was dried and 77 g were collected.

EXAMPLE 7

Methylaluminoxane (MAO) prepared according to Example 2 was used in the polymerization of ethylene. The polymerization was carried out as described in Example 6. The weight of dried polymer was 84.6 g.

EXAMPLE 8

Methylaluminoxane (MAO) prepared according to Example 4 was also employed in the polymerization of ethylene. The procedure described in Example 6 was closely followed. The resulting dried polyethylene weighed 110.5 g.

I claim:

1. A process for preparing a hydrocarbylaluminoxane comprising reacting a hydrocarbylaluminum compound with a hydrate of an alkali or alkaline earth metal hydroxide.

2. The process of claim 1 wherein the hydrate is $LiOH.1H_2O$.

3. The process of claim 1 wherein the reaction temperature is from about −20° C. to 60° C.

4. The process of claim 1 wherein the mole ratio of hydrocarbylaluminum to hydrate ranges from about 2:1 to 1:2.

5. The process of claim 4 wherein the mole ratio of hydrocarbylaluminum to hydrate is about 2:1.

6. The process of claim 4 wherein the mole ratio of hydrocarbylaluminum to hydrate is about 1:1.

7. A process for preparing methylaluminoxane comprising reacting a solution of trimethylaluminum in an inert hydrocarbon solvent with an alkali or alkaline earth metal hydroxide hydrate selected from lithium, sodium, potassium, barium, calcium, magnesium, and cesium hydroxide hydrate including mixtures thereof.

8. The process of claim 7 wherein the hydrate is $LiOH.1H_2O$.

9. The process of claim 7 wherein the reaction temperature is from about −20° C. to 60° C.

10. The process of claim 7 wherein the mole ratio of trimethylaluminum to hydrate ranges from about 2:1 to 1:2.

11. The process of claim 10 wherein the mole ratio of trimethylaluminum to hydrate is about 2:1.

12. The process of claim 10 wherein the mole ratio of trimethylaluminum to hydrate is about 1:1.

* * * * *

UNITED STATES PATENT AND TRADEMARK OFFICE
CERTIFICATE OF CORRECTION

PATENT NO. : 5,041,583
DATED : August 20, 1991
INVENTOR(S) : Samuel A. Sangokoya It is certified that error appears in the above-identified patent and that said Letters Patent is hereby corrected as shown below:

In the Claims: Column 4,

Claim 7, line 5, reads: -- sodium, potassium, barium, calcium, magnesium, and -- but should read: "sodium, potassium, barium, and"

Signed and Sealed this

Twenty-third Day of February, 1993

Attest:

STEPHEN G. KUNIN

*Attesting Officer*     *Acting Commissioner of Patents and Trademarks*